United States Patent
Scorza

(10) Patent No.: US 10,028,929 B2
(45) Date of Patent: Jul. 24, 2018

(54) METHOD OF TREATING RAYNAUD'S DISEASE SECONDARY TO CONNECTIVITIS USING AMINAPHTONE

(75) Inventor: Raffaella Scorza, Milan (IT)

(73) Assignee: LABORATORI BALDACCI S.P.A., Pisa (IT)

( * ) Notice: Subject to any disclaimer, the term of this patent is extended or adjusted under 35 U.S.C. 154(b) by 1427 days.

(21) Appl. No.: 13/005,902

(22) Filed: Jan. 13, 2011

(65) Prior Publication Data

US 2012/0022155 A1   Jan. 26, 2012

Related U.S. Application Data

(63) Continuation of application No. 12/296,872, filed as application No. PCT/IB2007/000921 on Apr. 10, 2007, now Pat. No. 8,202,903.

(30) Foreign Application Priority Data

Apr. 11, 2006 (IT) .............................. MI2006A0712

(51) Int. Cl.
*A61K 31/245* (2006.01)
(52) U.S. Cl.
CPC ................................. *A61K 31/245* (2013.01)
(58) Field of Classification Search
CPC .................................................... A61K 31/245
See application file for complete search history.

(56) References Cited

U.S. PATENT DOCUMENTS

| | | |
|---|---|---|
| 3,639,432 A | 2/1972 | Berti |
| 4,202,825 A | 5/1980 | Taya et al. |
| 5,043,323 A | 8/1991 | Bombardelli et al. |
| 5,648,377 A | 7/1997 | Bombardelli et al. |
| 5,858,330 A | 1/1999 | Boltri et al. |
| 6,835,401 B2 | 12/2004 | Soldati |
| 7,202,222 B2 | 4/2007 | Ramazanov et al. |

OTHER PUBLICATIONS

EPGOnline (http://www.epgonline.org/drugs/es/capilarema/, accessed Feb. 10, 2015, published Jan. 7, 2001).*
Romagna et al (Italian Dermatology and Syphilography Society Reunion, Genoa, Italian Journal of Dermatology, 111, 1976, pp. 148-151).*
Romagna et al (English Translation, 2015).*
Generic Drugs (http://www.ndrugs.com/?s=capilarema, accessed Feb. 10, 2015).*
Simonneau et al (Journal of the American College of Cardiology vol. 43, No. 12 Suppl S).*
Grader-Beck et al (Rheum Dis Clin N Am 31 (2005) 465-481).*
Pazienti (http://www.pazienti.net/en/diseases/connectivitis, accessed Jun. 2, 2015).*
Arthritis Foundation (http://www.arthritis.org/about-arthritis/types/raynauds-phenomenon/, accessed Apr. 11, 2017).*

(Continued)

*Primary Examiner* — Angela C Brown-Pettigrew
(74) *Attorney, Agent, or Firm* — Pearne & Gordon LLP

(57) ABSTRACT

The subject of the present invention is the use of aminaphtone for the preparation of a medicament for treating arteriophaties, in particular arteriophaties of a degenerative inflammatory type. Preferably, said medicament is formulated for oral administration.

8 Claims, 3 Drawing Sheets

(56) References Cited

OTHER PUBLICATIONS

Figure 1:
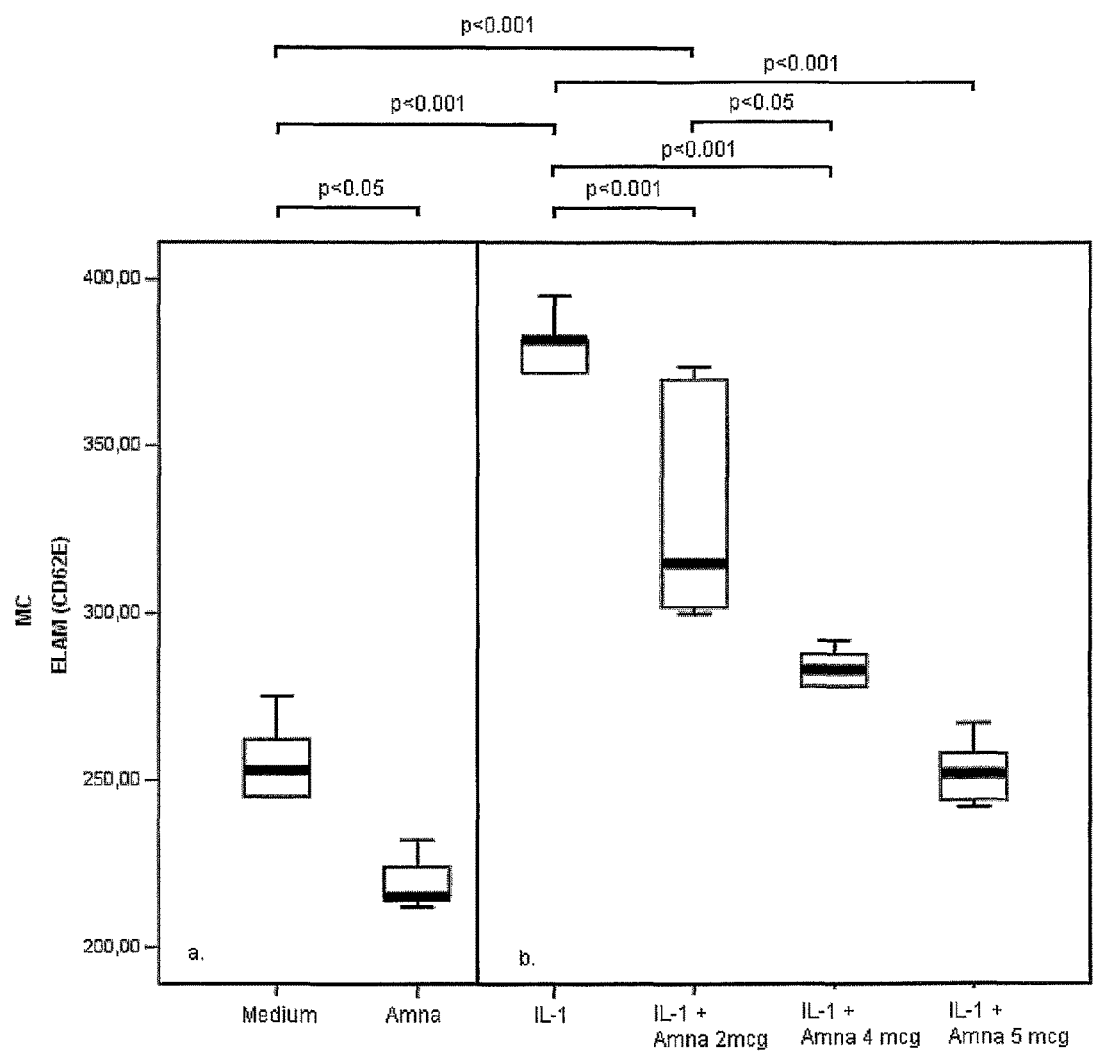

Grassi et al., "Increased capillary permeability in systemic sclerosis: help or hindrance?", Annals of Rheumatic Diseases, 1996; 55:603-606.
Beers, et al., "The Merck Manual of Diagnosis and Therapy", 17th Edition, Merck Research Laboratories, Whitehouse Station, N.J., 1999, pp. 1654-1657.
Villaverde C.A. et al., "Vascular Permeability Modification by Aminaftone", Revista de Farmacologia Clinica y Experimental, vol. 6, No. 1, 1989, pp. 9-14, XP009089752, ISSN: 0213-0157.
Romagna E. et al., "Preimi rilievi capillaroscopici sull'attivita del 2-idrossi-metil-1,4-naftoidrochinone-2-aminobenzoato o aminaftone", Giornale Italiano di Dermatologia / Minerva Dermatologica 1976, vol. 111, No. 2, 1976, pp. 148-151, XP009089770.
Boursier V., "Summary—Treatment of lymphedema: which drug?", Revue de Medecine Interne, CMR, Asnieres, FR, vol. 23, Jun. 2002, (Jun. 2002), pp. 421s-425s, XP004889120, ISSN: 0248-8663.
Beretta, Lorenzo et al., "Aminaphtone Down-Regulates Endothelin-1 Production in ECV-304 Cells: New Facts about an Old Drug", [Online], p. P-045, XP002452059, Retrieved from the Internet: URL:http://www.the-convention.co.jp/scleroderma/general.html> [retrieved on Sep. 20, 2007].
Romagna E. et al., "First Impressions by Capillarioscopy on the Activity of 2-Hydroxy-Methyl-1,4-Naphtohydroquinone-2-Aminobenzoate or Aminaphtone", Reunion of the S.I.D.E.S. in Genoa, Italian Journal of Dermatology 1976, pp. 1-6.
Shepherd et al., "Uncommon arteriopathies: what the vascular surgeon needs to know", Seminars in Vascular Surgery, vol. 16, Issue 3, Sep. 2003, pp. 240-251, Abstract retrieved from the Internet, Elsevier: Article Locator, Sep. 19, 2009, p. 1.
Scorza R. et al., "Effects of Aminaftone 75 mg TID on Soluble Adhesion Molecules: A 12-Week, Randomized, Open-Label Pilot Study in Patients with Systemic Sclerosis", Clinical Therapeutics, vol. 30, No. 5, May 2008, pp. 924-929.
Junger, M., et al., "Microcirculatory Dysfunction in Chronic Venous Insufficiency (CVI)", Microcirculation, vol. 7, Issue 51, Dec. 2000, p. S3-S12, 1 page, Abstract.
Miacek, B., et al., "Microcirculation Disturbances in Different Stages of Chronic Venous Insufficiency", Phlebologie, 2001; vol. 30, No. 11-5, 2001, 1 page, Abstract.
Morf, S., et al., "Microcirculation Abnormalities in Patients With Fibromyalgia—Measured by Capillary Microscopy and Laser Fluxmetry", Arthritis Res. Ther., vol. 7, R209-R216, 2005, 1 page, Abstract.
Bonetti, P., et al., "Endothelial Dysfunction a Marker of Atherosclerotic Risk", Arterioscler. Thromb. Vasc. Biol., vol. 23, p. 168-175, 2003, 1 page, Abstract.
Davignon, J., et al., "Role of Endothelial Dysfunction in Atherosclerosis", Circulation, vol. 109, [SUPPL III], III-27-III-32, 2004, 1 page, Abstract.
Beckett, V., et al., "Trial of Platelet-Inhibiting Drug in Scleroderma", Arthritis and Rheumatism, vol. 27, No. 10, Oct. 1984, pp. 1137-1143.
Van Der Meer, et al., "A Double-Blind Controlled Trial of Low Dose Acetylsalicylic Acid and Dipyridamole in the Treatment of Raynaud's Phenomenon", VASA-Suppl. 18, 1987, pp. 71-75.
Herrick, A.L., "Phathogenesis of Raynaud's Phenomenon", Rheumatology, vol. 44, 2005, pp. 587-596.
Goodfield, J.D., et al., "Whole Blood Platelet Aggregation and Coagulation Factors in Patients with Systemic Sclerosis", British Journal of Haematology, vol. 84, 1993, pp. 675-680.

* cited by examiner

METHOD OF TREATING RAYNAUD'S DISEASE SECONDARY TO CONNECTIVITIS USING AMINAPHTONE

The subject of the present invention is a novel use of the compound 2-hydroxy-3-methyl-1,4-naphthohydroquinone-2-p-aminobenzoate, known by the common name aminaphtone (hereinafter defined, by simplicity, as aminapthone), for the preparation of a medicament for treating arteriophaties; in particular, for the treatment, at the endothelial level, of arteriopathies of a degenerative inflammatory type.

Aminaphtone is a compound having a known pharmacological activity and commercially available in Italy and other countries for many years; in Italy, for example, it constitutes the active substance of the CAPILLAREMA drug, a medicine of Laboratori Baldacci S.p.A., Pisa. The ability of aminaphtone of acting on the venous capillary circulation, where it plays an action capable of normalizing the vasopermeability and increasing the capillary resistance in situations in which pathological conditions determine alterations of the microcirculation, is known.

In fact, the drug is widely used in the symptomatic treatment of chronic venous failure of the lower limbs, a situation in which the hematic stasis affects the microcirculation by producing alterations of the structure and the capillary functionality.

Pharmacological and clinical properties of this product have been published on scientific reviews and confirmed in these last years by the therapeutic use for the treatment of venous pathologies in countries where it is commercialized.

However, so far, the fact that aminaphtone also has the ability of antagonizing pathological events referable to an inflammatory state of the arterial vasal structure through different mechanisms than those currently known has never been shown.

In literature, it is known the importance of the endothelial component in the atherosclerosis, the diabetic microangiopathy, the Raynaud disease, the Buerger's disease, the obliterative arteriopathy, the systemic sclerosis, the connectivitis, the pulmonary hypertension and, in general, in all diseases characterized by an endothelial damage and/or vascular remodelling with a consequent tissue ischemia. In fact, the vascular endothelium results to be a system, consisting of metabolically active cells and responsive to physiological stimuli. Said stimuli control in a meticulous way the blood flow, acting a complex role in the control of vasoreactivity; platelet aggregation and the resistance to thrombi formation.

In order to adequately play their function, endothelial cells synthesize and secrete components of the connective tissue and molecules with an antagonist activity therebetween.

The endothelial inflammation is at the basis of degenerative/inflammatory pathologies, with an evolutionary character, with the presence of vacuolization, loss of endothelial integrity, perivascular infiltration of lymphocytes, macrophages, monocytes; fibroblasts, and increasing expression of adhesive molecules with the formation of a strong endogenous vasoconstrictor, such as endothelin, with a following hyperplasia of the intima, proliferation of smooth muscle cells of the vessels and a vascular remodelling.

In order to reduce this endothelial phlogistic-degenerative condition, there are today available some drugs, such as statins, which have however a double disadvantage: they are expensive therapies and determine, in an absolutely not negligible part of patients, a form of statin myopathy.

There are also currently available molecular analogues of the prostanoids (endoprost), which has the disadvantage of being extremely expensive drugs and not easy to administer with respect to administration routes, half-life of the molecule and side effects. Accordingly, there remains the need of being able to arrange novel and effective therapeutic means in order to fight against the endothelial inflammation of the arterial vascular system, thus reducing and/or eliminating the primary cause of arteriopathies, in particular of a degenerative type (accordingly obtaining a substantial-improvement or the complete resolution of the arterial disease).

The object of the present invention is to provide an answer to the need above pointed out.

These and other aims, which will result apparent from the following detailed description, have been attained by the Applicant, which has completely unexpectedly found that an opportune medicament including an effective quantity of aminapthone is able to give a proper answer to problems above pointed out.

An object of the present invention is the use of aminapthone for the preparation of a drug for treating artheriopathies, as reported in the appended independent claim.

Preferred embodiments of the present invention are reported in the appended dependent claims.

The present invention is shown in detail in the following description. Said invention is further shown also with the help of enclosed FIGS. 1 to 3, wherein:

FIG. 1: it graphically reports the inhibitory effect exerted by aminapthone, at different dosages, on the expression of the adhesive molecule E-selectine (ELAM-1) from human endothelial cells ECV 304. Specifically, FIG. 1 shows the density of membrane ELAM-1 fluorescence, determined through cytofluorometric analysis (mean channel) in different samples of ECV 304 cells, in the following conditions, respectively:

a.) in basal (Medium) and after a 48 hr incubation with basal medium additioned with aminapthone at a dosage of 4 mcg/ml (Amna);

b.) after incubation/activation for 48 hr with IL-1β at 100 U/ml (IL-1) and, respectively, IL-1 additioned with aminapthone (Amna) at concentrations of 2; 4; 5 mcg/ml.

Figure 2:
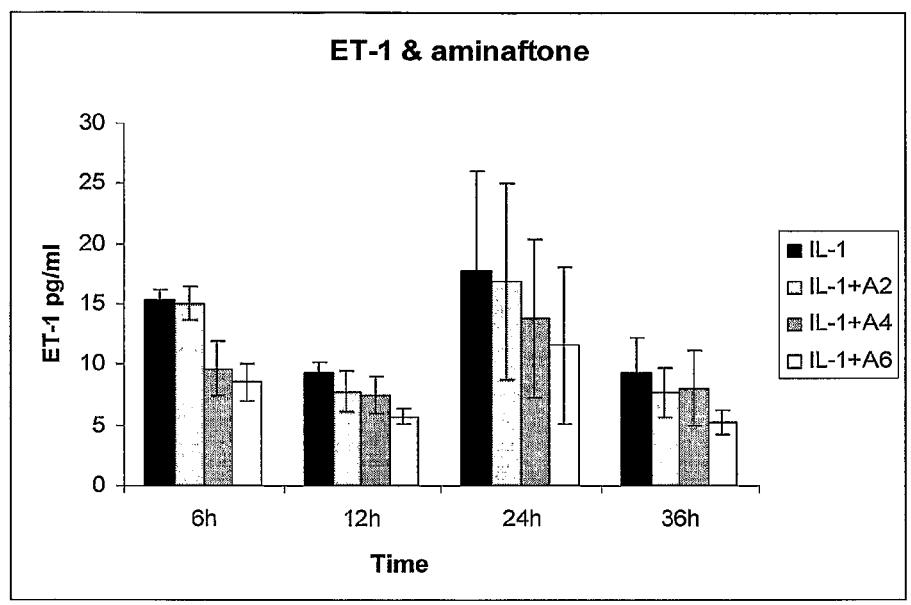

FIG. 2: it reports, in a block diagram, the inhibitory effect exerted by aminaphtone, at different dosages, on the endothelin production (ET-1) from human endothelial cells ECV 304 incubated/activated with IL-1β. Specifically, FIG. 2 shows the course of the ET-1 production, dosed with a specific EIA-Kit, in different samples of ECV 304 activated with IL-1β alone at 100 U/ml (IL-1) and, respectively, with IL-1 additioned with aminapthone at concentrations of 2, 4, 6 mcg/ml (A2; A4; A6).

Figure 3:
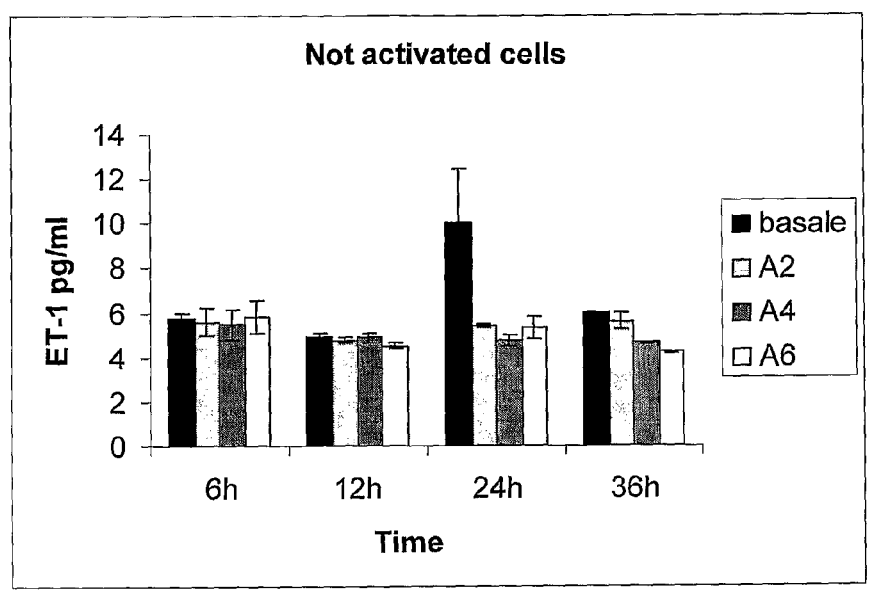

FIG. 3: it reports, in a block diagram, the inhibitory effect exerted by aminapthone, at different dosages, on the endothelin production (ET-1) from nonactivated human endothelial cells ECV 304. Specifically, FIG. 3 shows the course of the ET-1 production in different samples of ECV 304 non-activated with IL-1β but incubated with the culture medium (basal) alone, and, respectively, with basal medium additioned with aminapthone at concentrations of 2; 4; 6 mcg/ml (A2; A4; A6).

The present invention relates to the use of aminapthone for the preparation of a medicament for the treatment of arteriophaties; preferably, of all those types of arteriophaties referable to an inflammatory state of the arterial vasal structure; more preferably, of the endothelium.

In particular, said medicament could result suitable for the therapeutic treatment of: arteriosclerosis, atherosclerosis, obliterative arteriopathy, Raynaud disease secondary to connectivitis, primitive and secondary pulmonary hypertension, diabetic microangiopathy, Buerger's disease, systemic sclerosis and in all diseases characterized by endothelial damage and activation and consequent tissue ischemia.

The preparation of the medicament of the present invention is carried out in a traditional way by using, depending on the type of formulation that one wishes to prepare, preparative techniques known to the skilled in the pharmaceutical sector. Said preparation includes at least a step in which a therapeutically effective dose of active substance aminapthone, subject of the present invention, is additioned with a quantity of proper additives and excipients selected from: carriers, buffering agents, lubricants, dispersants, flavourings, sweeteners, stabilizers, preservatives, antioxidants commonly used in the pharmaceutical formulation technique. By mere way of absolutely not limiting example, amongst the particularly preferred excipients and additives there may be mentioned: starch, tween, flavours, such as those of mandarin, grapefruit, strawberry, bilberry, all fruits, sucrose, glucose, acesulfame, saccharin, aspartame, ascorbic acid, parabens, glutamine, arginine, superoxide dismutase, glutathione.

Said medicament can be administered to patients by different administration routes. A particularly preferred medicament of the present invention is formulated for oral administration.

Preferred compositions for oral administration are, for example, in form of capsules, beads, solutions or suspensions ready to drink, powders or granulates in sachets (to be suspended or dissolved in water or non-carbonated and non-alcoholic beverages at the time of use) or similar forms, tablets, effervescent formulations.

The medicament of the present invention can also be formulated in a coated, lacquered, encapsulated or microencapsulated form, so as to result gastroresistant.

Said medicament can also be formulated as a controlled-release form, so as to selectively release the active substances in the intestinal tract, particularly the colon.

However, other administration forms are not excluded, as a function of the type of patient and arteriopathy affection to be treated. In fact, also the formulation for parenteral or transdermic administration can be foreseen.

In a preferred embodiment of the invention, said medicament contains the active substance aminaphtone in a quantity between 30 and 150 mg/dose; preferably, from 50 to 100 mg/dose.

Said medicament is usually administered to the patient at a dosage between, on average, 75 and 450 mg/die; preferably, from 50 to 300 mg/die; more preferably, from 75 to 225 mg/die.

As pointed out in the following experimental section and the enclosed FIGS. 1 to 3, the medicament of the present invention, including aminapthone, has pointed out a direct protective effect of the arterial vascular endothelium through the block of cell and transcriptional mechanisms which are involved in the endothelial damage.

In the following experimental part, by way of example, there is shown a series of tests, carried out "in vitro", which confirm the effectiveness of aminapthone, provided by the pharmaceutical company Laboratori Baldacci S.p.A., in inhibiting the production, from inflamed arterial endothelial cells, of adhesive molecules and the strong endogenous vasoconstrictor endothelin.

Introduction

The aminapthone action has been studied in vitro on the E-selectine expression (hereinafter shown as ELAM-1) and on the endothelin-1 production (hereinafter shown as ET-1) from activated cells of ECV 304 line, activated and not with and without incubation with interleukin-1β (in short IL-1β). IL-1β represents a molecule also produced by humans in inflammation conditions and it is responsible for that series of alterations falling within the context of acute stage answers to stimuli.

ECV 304 cells are a human cell line presenting many features of endothelial cells and is commonly used for studying, in a standardized way, cell functions thereof.

The selection of parameters to be evaluated has been motivated by the determining role covered by the E-selectine expression in the premature stages of the endothelial phlogistic-degenerative injury. In humans, E-selectine expression covers an important role in arterial vascular pathologies by promoting the adhesion of platelets and the adhesion and the migration of inflammatory cells. On the contrary, the endothelin-1 production has been analyzed as it is fundamental in vasoconstriction and vascular remodelling processes typical of the endothelial injury. Endothelin-1 (ET-1) is in fact mentioned as one of the determining pathogenic principles of several human pathologies, for example: primitive and secondary pulmonary hypertension, secondary Raynaud disease, inflammatory arteriopathies and atherosclerosis; it further promotes the hypertrophic cardiomiopathy and the increase of the arterial pressure.

Materials and Methods

Dilution of Aminapthone.

0.5 g of powdered aminapthone (ex firm Baldadcci of Pisa, Italy) were dissolved in 5 ml of DMSO (dimethylsulfoxide); 50 μl of this solution were diluted in 5 ml of DMSO and, subsequently, 100 μl of this second solution were brought to 1 ml with PBS (phosphate buffer saline solution). Such solution in PBS was used as a parent solution to be diluted with the complete culture media in order to obtain final concentrations of aminapthone of 2, 4, 5 and 6 μg/ml, respectively, in the different experimental tests. The selection of such concentrations was carried out on the basis of in vivo therapeutic concentrations of the above mentioned drug Capillarema.

Cells.

Cell lines ECV 304: they are cells coming from umbilical cord of a female Japanese new-born and spontaneously immortalized at the $136^{th}$ step (distributed from Collection of Cell Cultures). Such cells were cultured in a complete medium consisted of: Medium 199, L-glutamine 1%, penicillin/streptomycin 10 (Invitrogen) with an addition of 10% FCS (fetal calf serum) (Hy-clone).

Cytofluorometric quantitative analysis of aminaphtone effects on the E-selectine adhesive molecule expression CD62 (ELAM-1).

Cells of the ECV304 line, cultured in 28 $cm^2$ Petri dishes, were stimulated with IL-1β at 100 U/ml (Roche) over 48 hrs in a complete medium and complete medium additioned with aminaphtone at the concentration of 2; 4; 5 μg/ml, respectively. Such concentrations are equivalent to concentrations reached "in vivo" through administration of Capillarema per os at the standard dosage of 3 capsules/day (capsules with 75 mg of active substance per day). Furthermore, cells untreated with IL-1β were incubated in a complete medium additioned with aminaphtone alone at the concentration of 4 μg/ml.

Samples, after washing with PBS, were removed from the culture plates through a treatment with trypsin-EDTA. Adhesive molecules expression was detected through incubation over 20 min. with 7 μl/$10^6$ of human monoclonal antibody CD62-E-PECy5 (ELAM-1) (Becton-Dickinson). The binding specificity was ensured by the addition of the control isotope. After washing and re-suspension in the fixing solution (1% paraformaldehyde, PFA in PBS), samples were analyzed in a flow cytometry with FACSdiva Software (Becton-Dickinson). Data were expressed as mean channel fluorescence and as fluorescence percentage of positive cells. All experiments were repeated 5 times on independent cell samples coming from different experimental sessions. Evaluation of endothelin production (ET-1).

a) EIA-kit—Supernatants of cell samples ECV304 were collected, cultured as above, treated with IL-1β at 100 U/ml over 6-12-24 and 36 hrs or with IL-1β at 100 U/ml additioned with aminaphtone at the concentration of 2; 4; 6 μg/ml, respectively. Moreover, samples non-stimulated with IL-1β were incubated with the addition of aminaphtone alone at 2; 4; 6 μg/ml.

The concentration of ET-1 existing in the supernatants was quantified through Endothelin-1 EIA-Kit (CAYMAN Chemical) in an interval between 0 and 250 pg/ml. This immunometric test is based on the "sandwich" technique with a double antibody.

b) Real-Time RT-PCR specific for Pre-Pro-ET-1 (PPET-1). The expression of PPET-1 gene was detected at 6-12-24-36 hrs, respectively, in samples: treated with IL-1β (100 U/ml); treated with IL-1β (100 U/ml) additioned with aminaphtone (2; 4; 6 μh/ml); non-stimulated by IL-1β but treated with aminaphtone alone. RT-PCR technique based on TaqMan technology was used (Applied Biosystems, Foster City, Calif.), through a sequence determination system ABI PRISM 7000 (Applied Biosystems). 2-4 μl were collected form each cDNA, diluted 1:5, in a final volume of 25 μl. PCR mix containing 1×TaqMan Universal PCR Master Mix with AmpoErase UNG enzyme; a specific primer and a probe FAM-labelled mix (Assay-On-Demand Gene Expression Products; Applied Biosystems). In the first amplification, the AmpliTaq Gold enzyme was activated over 10 min. at 95° C. All genes were then amplified: a first step of 15 sec. At 95° C.; a second step of 1 min. at 60° C.; all for 50 total cycles. The quantification of the specific mRNA PPET-1 was normalized for the constitutive gene expression glyceraldehyde-3-phosphate-dehydro-genase (GAPDH). Relative quantifications of the gene expression were made possible by the use of the comparative method CT ($\Delta\Delta CT$). The CT value was defined as the number of PCR cycles required for overcome the fluorescence signal (defined as 10-fold the standard deviation of the basal variation). The $\Delta CT$ value was defined as the difference between CT of mRNA PPET-1 and CT of mRNA GAPDH. The course of the mRNA PPET expression was computed according to the formula $2^{-(\Delta\Delta CT)}$, wherein $\Delta\Delta CT$ results to be the difference between each $\Delta CT$ and the $\Delta CT$ of the sample having the lowest mRNA (calibrator).

Statistical Analysis

For the statistical analysis, the analysis of variance was used (one-way ANOVA, ANalysis Of VAriance) through a software version 12.0 (SPSS Inc., Chicago, Ill.).

Comment of Results

Adhesive Molecules Expression

The cytofluorometric analysis has demonstrated that aminapthone is capable of reducing in a statistically significant way the E-selectine expression (ELAM-1) in ECV304 cells (MC: mean±standard deviation: 219±8.3; % positive cells 19.4±1.7) relative to cells incubated with the complete culture medium alone (MC: mean±standard deviation: 250±22 p<0.05; % positive cells 29.1±3.1; p<0.05). Furthermore, it has been shown that aminapthone inhibits, with a dose-dependent course, the expression of adhesive molecules in activated cells; (cells incubated with IL-1β 100 U/ml: MC: mean±standard deviation: 369.6±30.5; % positive cells: 38.4±3.7); (cells incubated with IL-1 β 100 U/ml in the presence of aminaphtone 2 mcg/ml: MC: mean±standard deviation: 332.2±36.8 p<0.001; % positive cells 36.6±4.5 p=n.s.); (cells incubated with IL-1p 100 U/ml in the presence of aminaphtone 4 mcg/ml: MC: mean±standard deviation: 278.4±16.2 p<0.001; % positive cells: 28.2±2.9 p<0.001); (cells incubated with IL-1β 100 U/ml in the presence of aminaphtone 5 mcg/ml: MC: mean±standard deviation: 252.6±10.3 p<0.001; % positive cells 27.2±3.7 p<0.001).

Results, expressed as fluorescence mean channel (MC) are reported in the enclosed FIG. 1 and confirm the inhibitory activity exerted by aminapthone on the expression of the E-selectine adhesion molecule.

Endothelin Production (ET-1)

EIA-kit confirms the trend, already observed at a level of gene transcription of PRE-PRO-ET-1, according to which aminapthone tends to reduce the ET-1 production from samples of ECV304 cells, both stimulated with IL-1 and incubated with the culture medium alone. Furthermore, it has been noted that such inhibition on ET-1 production resulted confirmed in all times and had a dose-dependent course. (FIGS. 2 and 3). The trend to a linear decrement of the ET-1 concentration in different times with increasing concentrations of aminapthone has reached a statistical significance in the following cases:

6 hours: IL-1β vs. IL-1β+aminapthone 4 mcg/ml: p<0.001; IL-1β vs. IL-1β+aminapthone 6 mcg/ml: p=0.000;

12 hours: IL-1β vs. IL-1β+aminapthone 4 mcg/ml: p<0.05; IL-1β vs. IL-1β+aminapthone 6 mcg/ml: p=0.000;

36 hours: IL-1β vs. IL-1β+aminapthone 6 mcg/ml: p=0.000.

As regards cells non-activated with IL-1 but incubated with the culture medium alone additioned with aminapthone at increasing concentrations, the statistical significance was reached in the following cases:

12 hours: basal medium vs. aminapthone 6 mcg/ml: p<0.05;

24 hours: basal medium vs. aminapthone 4 mcg/ml: p<0.05; basal medium vs. aminapthone 6 mcg/ml: p<0.05;

36 hours: basal medium vs. aminapthone 4 mcg/ml: p=0.000; basal medium vs. aminapthone 6 mcg/ml: p=0.000.

Obtained results are reported in the enclosed FIGS. 2 and 3 and confirm the inhibitory activity exerted by aminapthone on the endothelin-1 production.

Experimental results above shown confirm the novel use of aminapthone, according to what has been described and claimed in the present invention.

The invention claimed is:

1. A method for treating arteriopathies, wherein said arteriopathies is Raynaud's disease secondary to connectivitis, the method comprising the step of administering, to a subject in need thereof, a pharmaceutical composition comprising aminaphtone.

2. The method according to claim 1, wherein said pharmaceutical composition is administered by enteral or parenteral administration.

3. The method according to claim 2, wherein said pharmaceutical composition is administered via the oral route.

4. The method according to claim 1, wherein said pharmaceutical composition contains a quantity of active ingredient aminaphtone in a quantity between 30 and 150 mg/dose.

5. The method according to claim 3, wherein said pharmaceutical composition further includes a quantity of excipients selected from: carriers, buffering agents, lubricants, dispersants, flavourings, sweeteners, stabilizers, preservatives, antioxidants commonly used in the pharmaceutical formulation technique.

6. The method according to claim 1, wherein said pharmaceutical composition is administered in daily dose of between 30 and 350 mg/day.

7. The method according to claim 6, wherein said pharmaceutical composition is administered in daily dose of between 50 and 300 mg/day.

8. The method according to claim 7, wherein said pharmaceutical composition is administered in daily dose of between 75 and 250 mg/day.

* * * * *